United States Patent [19]
Williams

[11] Patent Number: 5,032,396
[45] Date of Patent: Jul. 16, 1991

[54] IL-7 TO STIMULATE PLATELET PRODUCTION

[75] Inventor: Douglas E. Williams, Redmond, Wash.

[73] Assignee: Immunex Corporation, Seattle, Wash.

[21] Appl. No.: 312,546

[22] Filed: Jan. 17, 1989

[51] Int. Cl.$^5$ ............................................. A61K 37/02
[52] U.S. Cl. .................................. 424/85.2; 424/85.1; 514/2; 514/8; 514/12; 514/21; 530/351
[58] Field of Search .................. 424/85.2, 85.1; 514/2, 514/8, 21, 12; 530/351

[56] References Cited

FOREIGN PATENT DOCUMENTS 260918  3/1988  European Pat. Off. .

OTHER PUBLICATIONS

*Exp Hematol.*, McDonald et al, vol. 15, 1987, pp. 719–721.
McDonald et al., *Exp Hematol.*, vol. 10, 1982, pp. 544–550.
McDonald et al, *Int. Journal Cell Cloning*, vol. 7, 1989, pp. 139–155.
Lu et al, *British J. Haemalology* 1988, vol. 70, pp. 149–156.
Lu et al, *Behring Matt.*, vol. 83 1988, pp. 181–187.
Hoffman et al, *Soc. Gen. Physiol Ser.* vol. 43, 1988, pp. 67–78.
Kuriya et al, *Blood Cells*, vol. 12, 1986, pp. 233–247.
Kawakita et al., "Apparent Heterogeneity of Human Megakaryocyte Colony- and Thrombopoiesis-Stimulating Factors." *Brit. J. Haematol.* 52:429–438 (1982).
Hoffman et al., "Assay of an Activity in the Serum of Patients with Disorders of Thrombopoiesis that Stimulates Formation of Megakaryocytic Colonies," *New Engl. J. Med.* 305:534 (1981).
Messner et al., "The Growth of Large Megakaryocyte Colonies from Human Bone Marrow," *J. Cell. Physiol. Suppl.* 1:45–51 (1982).
Kimura et al., "Human Megakryocytic Progenitors (CFU-M) Assayed in Methylcellulose: Physical Characteristics and Requirements for Growth," *J. Cell. Physiol.* 118:87–96 (1984).
Hoffman et al., "Purification and Partial Characterization of a Megakryocyte Colony-Stimulating Factor from Human Plasma," *J. Clin. Invest.* 75:1174–1182 (1985).
Namen et al. "Stimulation of B-Cell Progenitors by Cloned Murine Interleukin-," *Nature* 333:571 (1988).
Namen et al., "B Cell Precursor Growth-Promoting Activity," *J. Exp. Med.*, 167:988–1002 (1988).

*Primary Examiner*—Garnette D. Draper
*Attorney, Agent, or Firm*—Scott G. Hallquist; Jeffrey B. Oster; Christopher L. Wight

[57] ABSTRACT

Methods for stimulating platelet production in mammals, comprising administration of interleukin-7 (IL-7), are disclosed.

4 Claims, 2 Drawing Sheets

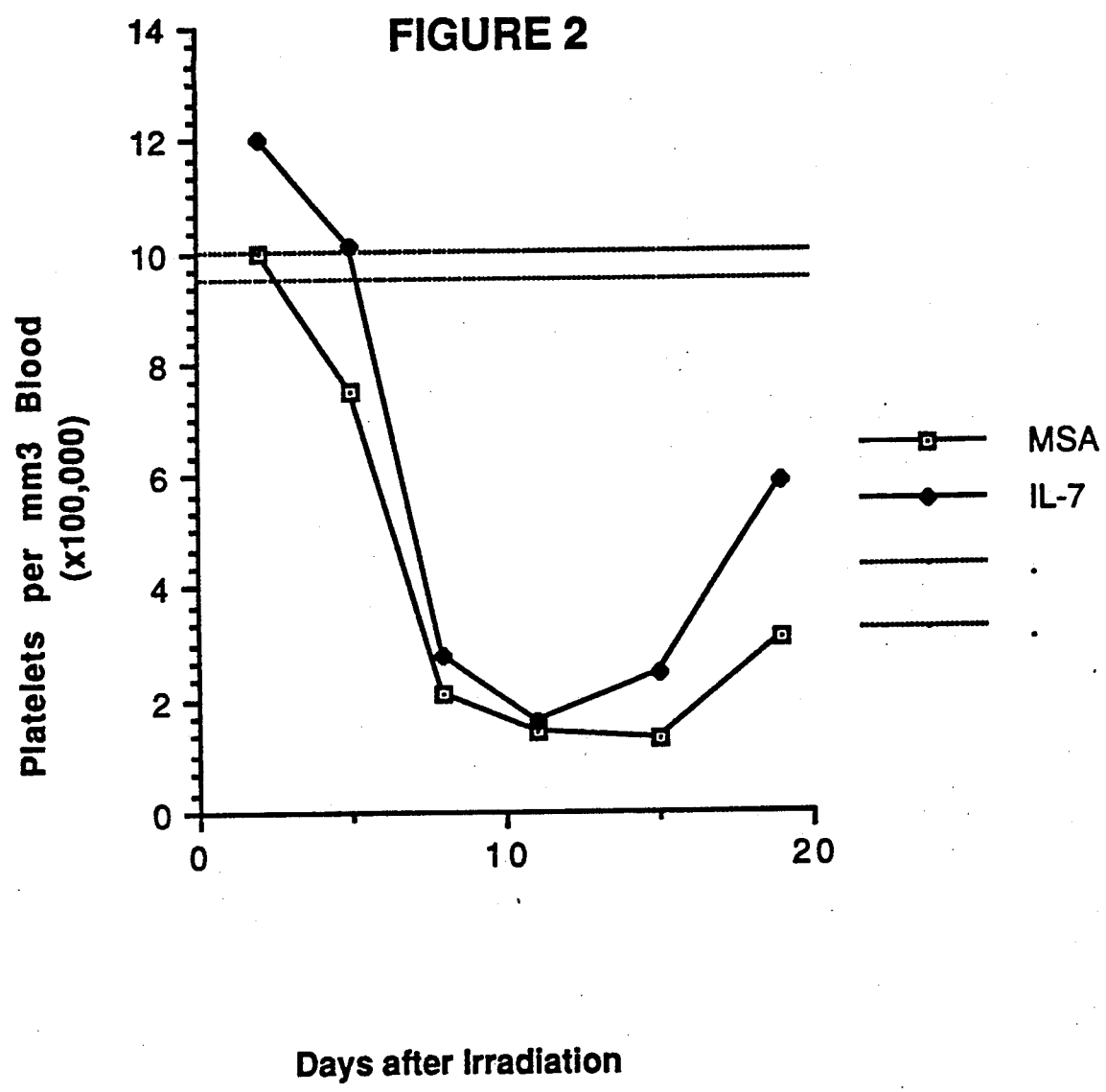

IL-7 TO STIMULATE PLATELET PRODUCTION

BACKGROUND OF THE INVENTION

The present invention relates generally to hematology and the molecular biology of blood growth factors, and specifically to the use of interleukin-7 in medicine as an inducer of megakaryocyte differentiation.

Megakaryocytes are the cellular source of platelets and arise from a common bone marrow precursor cell which gives rise to all hematopoietic cell lineages. The common precursor cell, known as the pluripotential hematopoietic stem cell, or PHSC, gives rise to the burst forming unit megakaryocyte (BFU-MK) which responds to IL-3 and tumor promoting phorbol esters (e.g., phorbol myristate acetate, PMA) in vitro, inducing development of large multi-focal colonies of megakaryocytes (MK). BFU-MK differentiate into MK colony forming cells (CFU-MK) which form colonies in vitro in response to IL-3, GM-CSF, EPO, G-CSF, IL-6 or IL-4, although evidence for the latter four is controversial. CFU-MK give rise to morphologically recognizable small MK which in the mouse stain with acetylcholinesterase (SAChE+ cells). It is unclear whether these cells have any proliferative potential remaining. SAChE+ cells then undergo a series of cytoplasmic and nuclear maturation steps (polyploidization) ultimately resulting in platelet producing MK. In vivo evidence suggests that the proliferative steps at the level of MK colony forming cells and the maturation steps resulting in platelet production are independently regulated by distinct cytokines.

Urine, serum and plsma from patients with hypomegakaryocytic thrombocytopenia have been shown to promote the formation of CFU-MK by bone marrow mononuclear cells in vitro. See, e.g., Kawakita et al., *Br. J. Haematol.* 52:429; Hoffman et al., *N. Engl. J. Med.* 305:533 (1981); Messner at al., *J. Cell. Physiol. Supp.* 1:45 (1982); and Kimura et al., *J. Cell. Physiol.* 118:87-96. None of these putative factors were purified to a significant degree.

Hoffman et al., *J. Clin. Invest.* 75:1174 (1985) reported purification of a megakaryocyte colony stimulating factor, designated Meg-CSF, from the sera of patients with hypomegakaryocytic thrombocytopenia. Ammonium sulfate precipitation, DEAE-cellulose chromatography, lectin affinity chromatography and RP-HPLC provided a glycoproteinaceous material which exhibited a molecular weight of about 46,000 daltons (da) and which stimulated the development of CFU-MK in bone marrow assays. This material has never been cloned or sequenced, and only modest effects in vivo have ever been reported.

Rosenberg, European Patent Application 260,918, discloses a putative "megakaryocyte stimulating factor" elaborated by human embryonic kidney cells which is alleged to be a specific hematopoietin for cells of the megakaryocyte lineage. The purified fraction disclosed in this reference was an "acidic protein" having an apparent molecular weight of about 15,000 in an assay in which protein synthesis by a partially purified megakaryocyte fraction and a rat promegakaryoblast cell line was determined. No in vivo studies were reported, and the extant literature has not reported further progress in cloning or sequencing this factor.

Interleukin-7 (IL-7), also known as lymphopoetin-1, is a lymphopoietic growth factor first isolated and cloned by virtue of its ability to stimulate growth of B and T cell progenitors in bone marrow. PCT Application U.S. Ser. No. 88/03747, filed Oct. 19, 1988, and European Patent Application No. 88309977.2, filed Oct. 24, 1988, (see also U.S. Ser. No. 07/113,566 now abandoned) disclose DNAs, vectors, and related processes for producing mammalian IL-7 proteins by recombinant DNA technology. The relevant disclosures of these patent applications are hereby incorporated by reference. The cloning of murine IL-7 was first reported by Namen et al., *Nature* 333:571 (1988) and human IL-7 by Goodwin et al., *Proc. Natl. Acad. Sci. USA* (in press). Purification of murine IL-7 from supernatants of a transformed bone marrow stromal cell line indicated an apparent molecular weight of approximately 25,000 da. See Namen et al., *J. Exp. Med.* 167:988 (1988). The cloned DNAs reported by Namen and Goodwin suggest minimum molecular weights for the murine and human molecules of 14,897 and 17,387 daltons, respectively, exclusive of any glycosylation.

It has now been found that IL-7 has the ability to significantly stimulate platelet production (thrombocytopoiesis) in vivo. This property of the molecule should render it a useful adjunct in therapy of patients suffering from acute thrombocytopenia, for example, as a result of chemo- or radiotherapy of various cancers. Currently, such patients are at grave risk when circulating platelet levels are depressed to levels wherein thrombogenesis is precluded. Conventional therapy for acute life-threatening thrombocytopenia involves repeated transfusions of purified platelets.

SUMMARY OF THE INVENTION

The present invention provides methods for inducing platelet production in a mammal in need thereof, comprising administering an effective amount of IL-7. In composition aspects, the invention provides compositions for inducing platelet production, comprising an effective quantity of IL-7 in admixture with pharmaceutically acceptable diluents, carriers or excipients, as well as methods of using IL-7 in preparing pharmaceutical compositions for inducing platelet production.

BRIEF DESCRIPTION OF THE FIGURES

FIG. 2 indicates the enhanced recovery of platelet levels which can be achieved when IL-7 is administered to irradiated mice. In FIG. 2, the horizontal dotted lines indicate platelet levels in normal control mice (n=14).

DETAILED DESCRIPTION OF THE PREFERRED ASPECTS OF THE INVENTION

Figure 1:
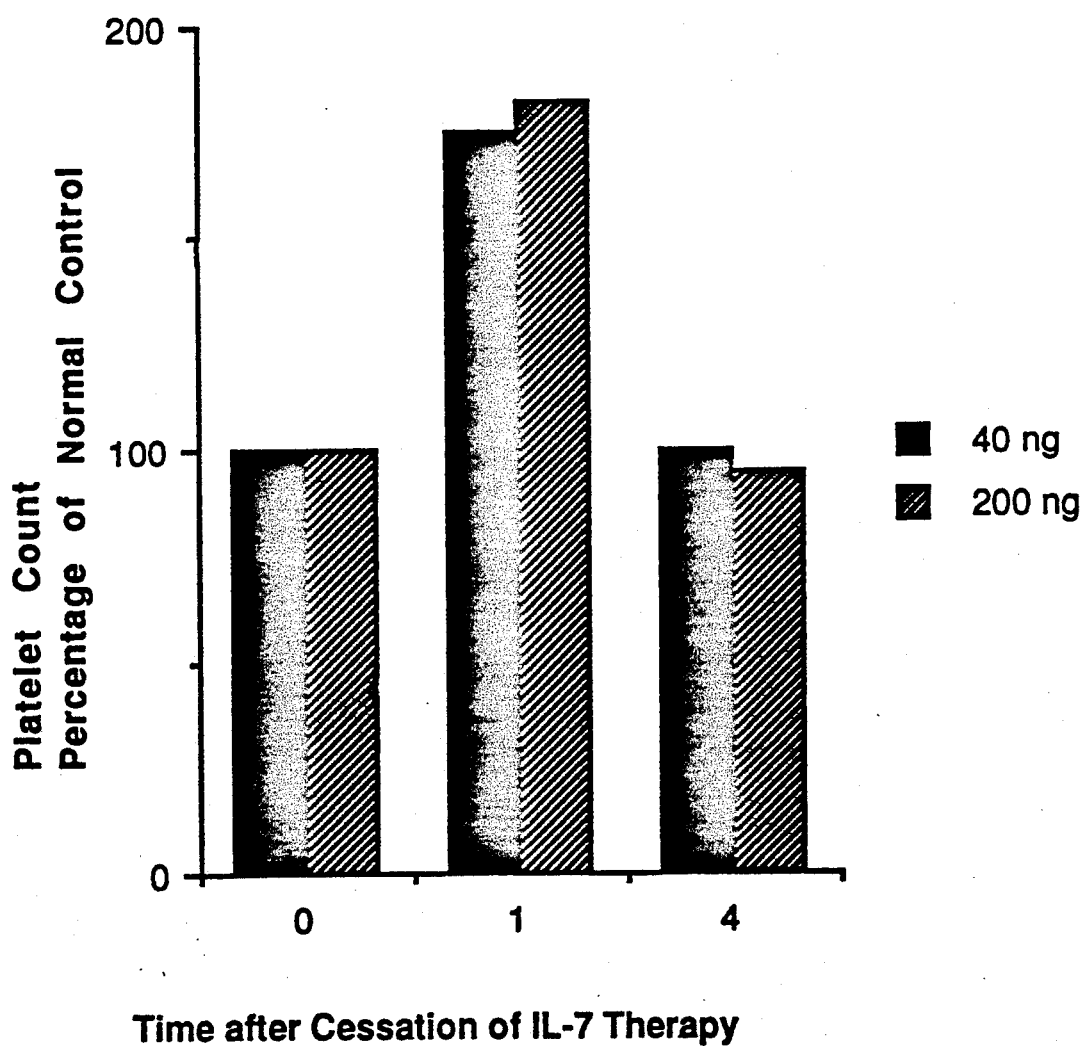
FIG. 1 indicates the increase in platelet count achieved when IL-7 is administered to normal mice.

For use in accordance with the methods of the present invention, IL-7 can be produced by any convenient method, for example, by expression in a mammalian cell line as described in the above-referenced patent applications relating to IL-7 proteins. The amino acid sequences of human and murine IL-7s are set forth in Tables 1 and 2, below:

TABLE 1

Human IL-7

| | ASP | CYS | ASP | ILE | GLU | 5 |

TABLE 1-continued

Human IL-7

| GLY | LYS | ASP | GLY | LYS | GLN | TYR | GLU | SER | VAL | LEU | MET | VAL | SER | ILE | 20 |
|---|---|---|---|---|---|---|---|---|---|---|---|---|---|---|---|
| ASP | GLN | LEU | LEU | ASP | SER | MET | LYS | GLU | ILE | GLY | SER | ASN | CYS | LEU | 35 |
| ASN | ASN | GLU | PHE | ASN | PHE | PHE | LYS | ARG | HIS | ILE | CYS | ASP | ALA | ASN | 50 |
| LYS | GLU | GLY | MET | PHE | LEU | PHE | ARG | ALA | ALA | ARG | LYS | LEU | ARG | GLN | 65 |
| PHE | LEU | LYS | MET | ASN | SER | THR | GLY | ASP | PHE | ASP | LEU | HIS | LEU | LEU | 80 |
| LYS | VAL | SER | GLU | GLY | THR | THR | ILE | LEU | LEU | ASN | CYS | THR | GLY | GLN | 95 |
| VAL | LYS | GLY | ARG | LYS | PRO | ALA | ALA | LEU | GLY | GLU | ALA | GLN | PRO | THR | 110 |
| LYS | SER | LEU | GLU | GLU | ASN | LYS | SER | LEU | LYS | GLU | GLN | LYS | LYS | LEU | 125 |
| ASN | ASP | LEU | CYS | PHE | LEU | LYS | ARG | LEU | LEU | GLN | GLU | ILE | LYS | THR | 140 |
| CYS | TRP | ASN | LYS | ILE | LEU | MET | GLY | THR | LYS | GLU | HIS | | | | 152 |

TABLE 2

Murine IL-7

| | | | | | | | | | | GLU | CYS | HIS | ILE | LYS | 5 |
|---|---|---|---|---|---|---|---|---|---|---|---|---|---|---|---|
| ASP | LYS | GLU | GLY | LYS | ALA | TYR | GLU | SER | VAL | LEU | MET | ILE | SER | ILE | 20 |
| ASP | GLU | LEU | ASP | LYS | MET | THR | GLY | THR | ASP | SER | ASN | CYS | PRO | ASN | 35 |
| ASN | GLU | PRO | ASN | PHE | PHE | ARG | LYS | HIS | VAL | CYS | ASP | ASP | THR | LYS | 50 |
| GLU | ALA | ALA | PHE | LEU | ASN | ARG | ALA | ALA | ARG | LYS | LEU | LYS | GLN | PHE | 65 |
| LEU | LYS | MET | ASN | ILE | SER | GLU | GLU | PHE | ASN | VAL | HIS | LEU | LEU | THR | 80 |
| VAL | SER | GLN | GLY | THR | GLN | THR | LEU | VAL | ASN | CYS | THR | SER | LYS | GLU | 95 |
| GLU | LYS | ASN | VAL | LYS | GLU | GLN | LYS | LYS | ASN | ASP | ALA | CYS | PHE | LEU | 110 |
| LYS | ARG | LEU | LEU | ARG | GLU | ILE | LYS | THR | CYS | TRP | ASN | LYS | ILE | LEU | 125 |
| LYS | GLY | SER | ILE | | | | | | | | | | | | 129 |

Various biologically active analogues of the foregoing proteins could also be employed in the methods and compositions of the present invention. As used herein, therefor, the term "IL-7" means proteins having substantial amino acid sequence identity to native mammalian IL-7s and equivalent biological activity, for example in standard bioassays or assays of IL-7 receptor binding affinity. Preferred methods for producing mammalian IL-7s involve expression in mammalian cells, although recombinant proteins can also be produced using insect cells, yeast, bacteria, or other cells under the control of appropriate promoters. Appropriate cloning and expression vectors for use with bacterial, fungal, yeast, and mammalian cellular hosts are described by Pouwels et al., *Cloning Vectors: A Laboratory Manual*, (Elsevier, New York, 1985), the relevant disclosure of which is hereby incorporated by reference. Various mammalian cell culture systems can be employed to express recombinat protein. Examples of mammalian expression systems include the COS-7 lines of monkey kidney fibroblasts, described by Gluzman, Cell 23:175 (1981), and other cell lines capable of expressing a compatible vector, for example, the C127, 3T3, CHO, HeLa and BHK cell lines. Mammalian expression vectors may comprise nontranscribed elements such as an origin of replication, a suitable promoter and enhancer, and other 5' or 3' flanking nontranscribed sequences, and 5' or 3' nontranslated sequences such as necessary ribosome binding sites, a polyadenylation site, splice donor and acceptor sites, and termination sequences. DNA sequences derived from the SV40 viral genome, for example, SV40 origin, early promoter, enhancer, splice, and polyadenylation sites may be used to provide the other genetic elements required for expression of a heterologous DNA sequence. Additional details regarding the use of mammalian high expression vectors to produce a recombinant mammalian IL-7 are provided below. Exemplary vectors can be constructed as disclosed by Okayama and Berg, *Mol. Cell. Biol.* 3:280 (1983), Cosman et al., *Nature* 312:768 (1984), Cosman et al., *Mol. Immunol.* 23:935 (1986), or Clark et al., U.S. Pat. No. 4,675,285.

Expression vectors are conveniently constructed by cleavage of cDNA clones at sites close to the codon encoding the N-terminal residue of the mature protein. For example, the murine cDNA can be cut with NdeI or ClaI, or the human cDNA with ClaI, to generate a fragment comprising substantially the entire coding region. Synthetic oligonucleotides can then be used to "add back" any deleted sections of the coding region and provide a linking sequence for ligation of the coding fragment in appropriate reading frame in the expression vector, and optionally a codon specifying an initiator methionine.

An alternative mammalian cell expression system for human IL-7 is assembled by inserting an IL-7 construction into a mammalian stable expression vector containing a selectable marker, which is then introduced into baby hamster kidney (BHK) cells. The expression vector is constructed as follows. A SmaI-HincII cDNA fragment is excised from the pDC201/hIL-2R/hIL-7 plasmid described in PCT Application U.S. Ser. No. 88/03747 and European Patent Application No. 88309977.2, (see above) and cloned into the repaired (Klenow polymerase) BamH1 site of a mammalian expression vector, pNPV1, which comprises an SV40 origin of replication and viral enhancer sequences attached to a mouse metallothionein promoter (MT-1). This hybrid promoter displays a high level of stable, constitutive expression in a variety of mammalian cell types. pNPV1 also contains the normal dihydrofolate reductase (DHFR) DNA sequence which enables methotrexate selection for mammalian cells harboring this plasmid. DHFR sequence amplification events in such cells can be selected by using elevated methotrexate concentrations. In this way, one also generally amplifies the contiguous DNA sequences and thus achieves enhanced expression.

Selection and expression are conducted using adherent BHKtk-ts 13 cells (ATCC CRL 1632), described by Waechter, et al., *Proc. Natl. Acad. Sci. USA* 79:1106 (1982), and Talavera, et al., *J. Cell Physiol.* 92:425 (1977). These cells are capable of both high mannose and complex oligosaccharide protein modification. After linearization of the expression plasmid with Sal1, the DNA is introduced into BHK cells by electroporation at 300 volts at 960 microfarads. Suitable electoporation techniques are disclosed by Ausubel et al, eds., *Current Protocols in Molecular Biology*, (Wiley-Interscience, Media, PA, USA), at 9.3.1. After 48 hours, 1 micromolar methotrexate is introduced into the culture medium and resistant colonies are selected after a two week period. Representative clones are bioassayed for secretion of hIL-7 into the culture supernatant fraction. The highest expressing clones are then subjected to further selection regimes using 10, 20 and 50 micromolar methotrexate. Resistant colonies are further analyzed to identify high expression level clones. The BHK lines selected using this protocol are adherent cells and scale-up production schemes can be devised involving either suspension growth using beads or growth in bioreactors using hollow fibre technology. BHK cells can be readily adapted to growth as suspension cells.

IL-7 can be purified for administration from cell culture supernatants as follows. Supernatants are concentrated using a commercially available protein concentration filter, for example, an Amicon ® (W. R. Grace & Co., Danvers, MA, USA) or Pellicon ® (Millipore Corp., Bedford, MA, USA) ultrafiltration unit. Following the concentration step, the concentrate can be applied to a suitable anion exchange resin, for example, a matrix or substrate having pendant diethylaminoethyl (DEAE) groups. The matrices can be acrylamide, agarose, dextran, cellulose or other types commonly employed in protein purification. A preferred matrix is DEAE-Sephacel ® (Pharmacia). When media containing DEAE groups are employed, extracts containing IL-7 are applied at a weakly basic pH (e.g., pH 8) and at a sodium chloride concentration (or other suitable salt) of about 100 mM. Many contaminating proteins are bound by the ion exchanger, while IL-7 is recovered in unbound fractions. Following anion exchange chromatography, a cation exchange step can be employed. In this step, IL-7containing fractions are applied to a cation exchanger at weakly acid conditions with low salt (e.g., pH 5, 100 mM NaCl). IL-7 is bound by the exchanger and can be eluted in a more highly purified form at higher salt concentrations and at weakly basic pH. Suitable cation exchangers include various insoluble matrices comprising sulfopropyl or carboxymethyl groups. Sulfopropyl groups are preferred. A useful material for IL-7 purification is SP-Trisacryl ® (Pharmacia-LKB). Following cation exchange chromatography, an affinity step employing a matrix having a blue dye ligand has been shown to be useful. Suitable dye ligands include Blue B, which can be obtained as a conjugate with agarose (Blue B agarose). Other dye ligand equivalents can also be employed. Finally, one or more reversed-phase high performance liquid chromatography (RP-HPLC) steps employing hydrophobic RP-HPLC media, e.g., silica gel having pendant methyl or other aliphatic groups, can be employed to further purify a IL-7 composition. Some or all of the foregoing purification steps, in various combinations, can also be employed to provide a homogeneous recombinant protein suitable for pharmaceutical formulation.

In composition and method-of-use aspects, the present invention provides therapeutic compositions comprising an effective amount of any of the mammalian IL-7 proteins of the invention and a suitable diluent or carrier, and methods for stimulating megakaryocyte development or proliferation or modulating or augmenting platelet production in mammals, including humans, comprising administring an effective amount of any of the foregoing compositions. Use in conjunction or admixture with other lymphokines, e.g., IL-1α, IL-1β, IL-2, IL-3, IL-4, IL-5, IL-6, CSF-1, GM-CSF, G-CSF, EPO, IFN-α, IFN-β or IFN-γ is also contemplated.

For therapeutic use, a purified IL-7 is administered to a mammal for treatment in a manner appropriate to the indication. Thus, for example, a mammalian IL-7 composition administered as a stimulator of platelet production or function can be given by bolus injection, continuous infusion, sustained released from implants, or other suitable technique. Typically, an IL-7 therapeutic will be administered in the form of a composition comprising purified protein in conjunction with physiologically acceptable carriers, excipients or diluents. Neutral buffered saline or saline mixed with conspecific serum albumin are exemplary appropriate diluents. Preferably, product is formulated as a lyophilizate using appropriate excipient solutions (e.g., sucrose) as diluents. Appropriate dosages can be determined in trials; generally, dosages of 10 ng to 100 μg/kg/day, preferably 100 ng to 1 μg/kg/day for 1–20 days, can be expected to induce a biological effect. For example, bolus injections of 1 μg/kg can be given at 4-day intervals as a stimulator of platelet production.

The following examples demonstrate the utilities of the methods and compositions of the present invention.

EXAMPLE 1

Induction of MK Maturation by IL-7

A human marrow cell line, designated EST-IU, was derived from a patient with acute non-lymphocytic leukemia and a mediastinal germ-cell tumor. Marrow from the patient was placed in culture on a lung fibroblast feeder layer and eventually was weaned from the feeder cells. The cells were frozen in liquid nitrogen at each cell passage and the progeny of one such passage were employed in the following experiment. The cells exhibit a phenotype, including polyploidy, consistent with human MK. Treatment of the cells with PMA results in a shift to higher ploidy value and enhanced expression of platelet-associated antigens consistent with maturation toward a platelet producing MK phenotype.

To evaluate IL-7 effects, EST-IU cells were set up in 3 day liquid cultures with media alone, $5 \times 10^{-8}$M PMA, or 3000 U/ml (pre-B cell proliferation assay) purified murine IL-7. The media employed was RPMI 1640 supplemented with 10% V/V fetal bovine serum. Cells were suspended at a concentration of $2 \times 10^5$ cells in 1 ml medium. After 3 days, cells were harvested, washed and contacted with a saturating concentration of mouse anti-human platelet glycoprotein Ib (GpIb) followed by goat anti-mouse fluorescein isothiocyanate (FITC) conjugated anti-IgG (Fab fragment). After extensive washing, cells were analyzed by flow cytometry. GpIb is expressed on relatively mature MK but is absent on the earliest recognizable MKs. The results indicated the PMA, as anticipated, induced enhanced expression of GPIb from 21% in media control cells, to 67% positive following PMA treatment. IL-7 treated cells were induced to 61% positive for GpIb expression.

EXAMPLE 2

IL-7 Effects upon Circulating Platelets in Normal Mice

Normal C57B1/6 mice were injected twice daily with either 20 or 100 ng IL-7 or murine serum albumin (MSA) as control for 5 days. Cardiac blood platelet counts were determined microscopically with a Unopette ® system 1 and 4 days after cessation of therapy. The number of circulating platelets was significantly ($p=0.001$) greater in the IL-7 treated animals (4-5 animals per group) than in the MSA-treated controls one day after therapy, returning to normal levels at day 4. The results are depicted graphically in FIG. 1.

EXAMPLE 3

IL-7 Effects in Sublethally Irradiated Mice

Normal C57B1/6 mice were irradiated to a level of 750 rads using a $^{137}$Cs source on day zero, and injected with 1 μg IL-7 or MSA daily (2×500 ng injections). Platelet counts from cardiac or retroorbital blood were then determined as above for MSA control, IL-7-treated, and non-irradiated control mice, with 4–10 mice per treatment group and 14 mice in the non-irradiated control group. The results are depicted in FIG. 2, and indicate that IL-7 delayed the onset of acute radiation-induced thrombocytopenia, and accelerated recovery of platelet levels following a nadir on day 11. Average platelet counts between IL-7 and MSA treated groups were statistically significantly different on all days except days 8 and 11.

The present invention is not intended to be limited to the foregoing specific embodiments, and encompasses all compositions and methods within the scope of the following claims.

I claim:

1. A method for inducing platelet production in a mammal in need thereof, comprising administering an effective amount of IL-7.

2. A method according to claim 1, wherein the mammal is a human.

3. A method according to claim 2, wherein the IL-7 is human IL-7.

4. The method of claim 1 wherein the amount of IL-7 administered is from about 10 ng/kg/day to about 100 μg/kg/day.